US012668050B2

(12) United States Patent     (10) Patent No.: US 12,668,050 B2
Bäck et al.                              (45) Date of Patent: Jun. 30, 2026

(54) METHOD OF MANUFACTURING AN ABSORBENT CORE FOR A DISPOSABLE ABSORBENT HYGIENE ARTICLE

(71) Applicant: Essity Hygiene and Health Aktiebolag, Gothenburg (SE)

(72) Inventors: Lucas Bäck, Gothenburg (SE); Cleiton Aparecido Ribeiro De Souza, Jarinu (BR); Montserrat Martinez Estela, Puigpelat (ES); Fanny Stenholm, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 18/841,757

(22) PCT Filed: Feb. 28, 2022

(86) PCT No.: PCT/EP2022/054991
§ 371 (c)(1),
(2) Date: Aug. 27, 2024

(87) PCT Pub. No.: WO2023/160823
PCT Pub. Date: Aug. 31, 2023

(65) Prior Publication Data
US 2025/0162302 A1     May 22, 2025

(51) Int. Cl.
*A61F 13/15*       (2006.01)
*B32B 37/10*       (2006.01)
(Continued)

(52) U.S. Cl.
CPC ...... *B32B 37/1284* (2013.01); *A61F 13/1565* (2013.01); *A61F 13/15658* (2013.01);
(Continued)

(58) Field of Classification Search
None
See application file for complete search history.

(56) References Cited

U.S. PATENT DOCUMENTS

| | | | |
|---|---|---|---|
| 4,790,839 | A | 12/1988 | Ahr |
| 5,007,906 | A | 4/1991 | Osborn et al. |

(Continued)

FOREIGN PATENT DOCUMENTS

| | | |
|---|---|---|
| CL | 43780 | 10/2001 |
| CL | 43887 | 10/2002 |

(Continued)

OTHER PUBLICATIONS

International Search Report (PCT/ISA/210) and Written Opinion (PCT/ISA/237) mailed on Nov. 4, 2023 by the European Patent Office as the International Searching Authority for International Application No. PCT/EP2022/085622. (14 pages).

(Continued)

*Primary Examiner* — Barbara J Musser
(74) *Attorney, Agent, or Firm* — BUCHANAN INGERSOLL & ROONEY PC

(57) ABSTRACT

A method of manufacturing an absorbent core for a disposable absorbent hygiene article includes providing a first core cover web and at least one pleat in the first core cover web; applying an adhesive to the pleated first core cover web; bringing the pleated first core cover web into conformance with a recess, the recess including at least one channel-forming element arranged on a bottom surface of the recess and causing the pleat to at least partially unfold at the channel-forming element; applying absorbent material on the first core cover web in the recess; applying an adhesive on a second core cover web; applying the second core cover web to the first core cover web; forming an absorbent laminate by pressing together the second and first core cover webs; and forming individual absorbent cores by severing
(Continued)

the absorbent laminate. An absorbent core and an absorbent article including the absorbent core are also disclosed.

15 Claims, 5 Drawing Sheets

(51) Int. Cl.

| | | |
|---|---|---|
| *B32B 37/12* | (2006.01) | |
| *B32B 37/20* | (2006.01) | |
| *B32B 38/00* | (2006.01) | |

(52) U.S. Cl.
CPC ........ *A61F 13/15682* (2013.01); *B32B 37/10* (2013.01); *B32B 37/20* (2013.01); *B32B 38/004* (2013.01); *B32B 2555/02* (2013.01)

(56) References Cited

U.S. PATENT DOCUMENTS

| | | | |
|---|---|---|---|
| 5,358,500 | A | 10/1994 | Lavon et al. |
| 5,527,303 | A | 6/1996 | Milby et al. |
| 5,756,039 | A | 5/1998 | McFall et al. |
| 6,372,952 | B1 | 4/2002 | Lash et al. |
| 8,708,988 | B2 | 4/2014 | Ng |
| 2001/0029359 | A1 | 10/2001 | Carlucci |
| 2007/0043330 | A1 | 2/2007 | Lankhof et al. |
| 2010/0100065 | A1 | 4/2010 | De et al. |
| 2010/0280474 | A1 | 11/2010 | Bruzadin et al. |
| 2014/0276511 | A1 | 9/2014 | Bauduin et al. |
| 2014/0371701 | A1 | 12/2014 | Bianchi et al. |
| 2015/0045756 | A1 | 2/2015 | Wright et al. |
| 2015/0080821 | A1 | 3/2015 | Peri et al. |
| 2015/0173977 | A1 | 6/2015 | Stelzig et al. |
| 2015/0342796 | A1 | 12/2015 | Bianchi et al. |
| 2017/0312146 | A1 | 11/2017 | Bianchi et al. |
| 2020/0276059 | A1 | 9/2020 | Smet et al. |
| 2025/0213400 | A1 | 7/2025 | Bäck et al. |

FOREIGN PATENT DOCUMENTS

| | | | |
|---|---|---|---|
| CL | 2015003597 | A1 | 9/2016 |
| CL | 2016000640 | A1 | 11/2016 |
| CL | 2016001567 | A1 | 1/2017 |
| CN | 106255484 | A | 12/2016 |
| CO | 6330158 | A1 | 10/2011 |
| EP | 1974705 | A1 | 10/2008 |
| EP | 2586412 | A1 | 5/2013 |
| EP | 2870951 | A1 | 5/2015 |
| EP | 2949299 | A1 | 12/2015 |
| JP | 2012081246 | A | 4/2012 |
| JP | 2014530693 | A | 11/2014 |
| JP | 2017516542 | A | 6/2017 |
| JP | 2019205917 | A | 12/2019 |
| MX | PA01011092 | A | 9/2004 |
| MX | 2016015558 | A | 3/2017 |
| WO | 9955269 | A1 | 11/1999 |
| WO | 0236059 | A1 | 5/2002 |
| WO | 2012035787 | A1 | 3/2012 |
| WO | 2014007043 | A1 | 1/2014 |
| WO | 2016207444 | A1 | 12/2016 |
| WO | 2019125231 | A1 | 6/2019 |
| WO | 2021215972 | A1 | 10/2021 |

OTHER PUBLICATIONS

International Search Report (PCT/ISA/210) and Written Opinion (PCT/ISA/237) mailed on Oct. 18, 2022 by the European Patent Office as the International Searching Authority for International Application No. PCT/EP2022/054991. (12 pages).

Office Action issued on Dec. 10, 2025, by the Colombian Patent Office in corresponding Colombian Patent Application No. NC2024/0011516, and a partial English Translation of the Office Action. (12 pages).

Office Action issued on Dec. 5, 2025, by the Canadian Patent Office in corresponding Canadian Patent Application No. 3,253,448. (4 pages).

Office Action issued on Dec. 4, 2025, by the Mexican Patent Office in corresponding Mexican Patent Application No. MX/a/2024/010513, and a machine English Translation of the Office Action. (16 pages).

Office Action (Notice of Reasons for Rejection) issued on Sep. 30, 2025, by the Japanese Patent Office in corresponding Japanese Patent Application No. 2024-550733, and an English Translation of the Office Action. (15 pages).

Office Action (Notice of Reasons for Rejection) issued on Jul. 1, 2025, by the Japanese Patent Office in corresponding Japanese Patent Application No. 2024-550861, and an English Translation of the Office Action. (8 pages).

Office Action issued on Jul. 31, 2025, by the Chilean Patent Office in corresponding Chilean Patent Application No. 2024-02520, and an English Translation of the Office Action. (17 pages).

Office Action issued on Jun. 19, 2025, by the Chilean Patent Office in corresponding Chilean Patent Application No. 2024-02572, and an English Translation of the Office Action. (28 pages).

Office Action issued on Feb. 5, 2026, by the Chilean Patent Office in corresponding Chilean Patent Application No. 20242520, and a machine English Translation of the Office Action. (30 pages).

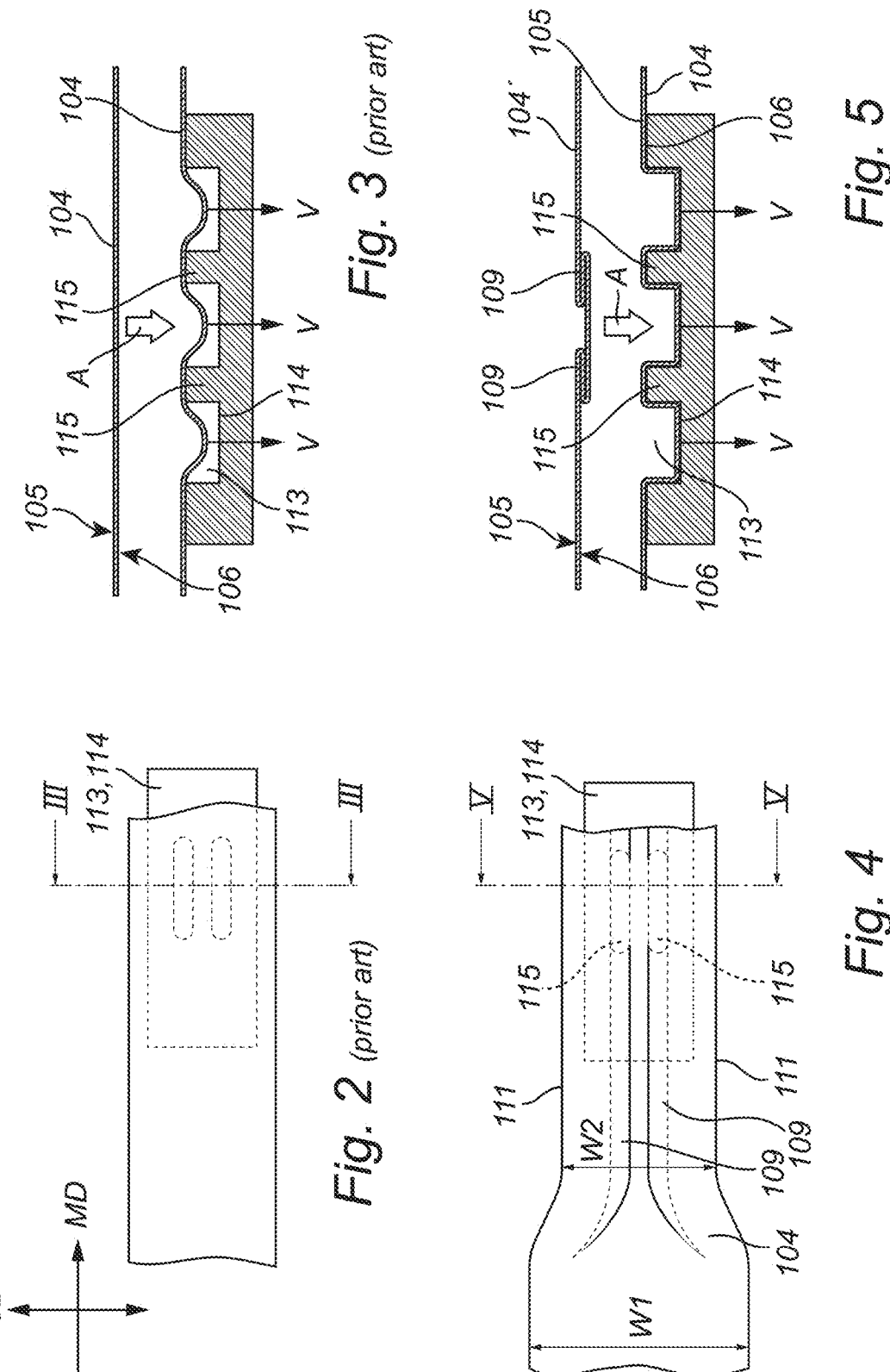

METHOD OF MANUFACTURING AN ABSORBENT CORE FOR A DISPOSABLE ABSORBENT HYGIENE ARTICLE

TECHNICAL FIELD

The disclosure pertains to a method of manufacturing an absorbent core for a disposable absorbent hygiene article involving providing a first core cover web, applying an absorbent material by mat-forming on the first core cover web and attaching a second core cover web to the first core cover web and the absorbent material, thereby sandwiching the absorbent material between the first core cover web and the second core cover web. The disclosure further pertains to an absorbent core produced according to the method and an absorbent article including the absorbent core.

BACKGROUND

In disposable absorbent articles, such as baby diapers and other articles for absorption of body fluids such as pant-type absorbent garments, incontinence protectors and sanitary napkins, there is a conflict between the requirement of sufficient absorption capacity and leakage security on the one hand and wearer comfort and discretion on the other hand. Accordingly, there is a demand for highly absorbent articles which are non-bulky and flexible, and which conform well to the body of a wearer. It is highly desirable that the wearer does not feel restricted or uncomfortable when wearing the absorbent article while still being confident that the article is efficient in preventing leakage. For adult user's it is particularly important that a pant-type garment resembles ordinary underwear as closely as possible and can be inconspicuously worn under normal tightfitting clothing. To provide sufficient absorption capacity while offering thin absorbent articles, a large proportion of the absorbent material may be what is commonly known as superabsorbent material or merely "superabsorbents". The superabsorbents may be combined with absorbent fibers, predominantly cellulose pulp fibers, creating a fibrous network which contributes to distribute liquid in the absorbent core and to retain particulate superabsorbent material in the core. Superabsorbents are polymeric materials usually incorporated in absorbent articles in the form of fibers, particles, or granules. Superabsorbents can absorb many times their own weight of fluid upon swelling and formation of a hydrogel. Absorbent articles which contain a large amount of superabsorbent material have been found to lose their initial flexibility and wearer comfort as they absorb liquid and swell. High-impact areas of an absorbent article, such as the crotch portion of a diaper which contains a large amount of absorbent material distributed over a relatively small area may grow thick and become stiff as the article absorbs liquid. Moreover, it is a concern in disposable absorbent articles that the available absorption capacity of the absorbent material may be utilized as fully as possible, to keep material consumption at a minimum when producing the absorbent articles. It is therefore desirable that the full absorbent capacity of the superabsorbents can be utilized.

In WO2021/215972 A1 it has been suggested to arrange channels in the form of absorbent material free areas in an absorbent core sandwiched between a liquid-permeable upper core cover layer and a lower core cover layer. The upper core cover layer and the lower core cover layer are attached to each other within at least two spaced-apart attachment zones in the absorbent material free areas.

The attachments between the upper core cover layer and the lower core cover layer in the absorbent material free areas prevents absorbent material from moving freely in the absorbent core and become redistributed in an uncontrolled and undesired manner between the upper core cover layer and the lower core cover layer. During use of the absorbent article, the absorbent core will absorb body fluid and swell. The attachment zones in which the upper core cover layer and the lower core cover layer are connected with each other constitute restriction means which limit swelling in a thickness direction of the absorbent article by prohibiting the upper core cover layer and the lower core cover layer from freely moving away from each other. When the absorbent core absorbs fluid and swells, the absorbent material on either side of an absorbent material free area can expand in the transverse direction of the absorbent article into the parts of the absorbent material free area which are located between the attachment zones.

Although the absorbent cores in WO2021/215972 A1 have been found to improve utilization of the available absorption capacity in the absorbent cores, the expansion room for the swelling absorbent material is limited by the available space in the absorbent free areas.

Furthermore, channels are commonly arranged in an absorbent core to promote liquid acquisition and distribution in the core. In the absorbent cores in WO2021/215972 A1, the channels formed by the absorbent material free areas are at least partially obliterated over time as the absorbent material swells into the channels and reduces their ability to receive and distribute body liquids.

Absorbent cores are commonly sandwiched between a lower core cover layer and an upper core cover layer, the cores being mat-formed onto the lower core cover layer and subsequently covered with the upper core cover layer. Channels may be formed in the core by arranging raised channel-forming elements on the mat-forming surface of a mat-former and applying the lower core cover layer over the channel-forming elements. The lower core cover layer is brought to conform to the raised channel-forming elements and it has been found that there is a risk that the lower core cover layer while being applied to the channel-forming elements becomes torn by corners or edges on the raised channel-forming elements.

An object of the present disclosure is to provide an improved method for manufacturing an absorbent core having one or more channels arranged therein. A further object of the present disclosure is to provide an absorbent core having improved ability of utilizing the available absorption capacity of the absorbent material in the core. Yet a further object of the present disclosure is to provide an absorbent core having improved ability of utilizing the available absorption capacity of the absorbent material in the core.

SUMMARY

The above, and further objects may be achieved with a method according to claim 1, an absorbent core according to claim 14. Variations of the disclosure are set out in the dependent claims and in the following description.

The absorbent articles referred to herein may be wearable disposable absorbent articles, for example in the form of open diapers, pant diapers, belted diapers, incontinence garments, feminine hygiene garments and the like, as well as disposable absorbent inserts, e.g., incontinence shields or sanitary napkins, which are worn inside a support garment, such as a support pant or ordinary underwear. The articles are used to absorb, distribute, and store various types of body exudates while providing a high level of comfort and a sense of dryness to the wearer during wearing.

A method of manufacturing an absorbent core for a disposable absorbent hygiene article as disclosed herein comprises;

providing a first core cover web having a first surface and a second surface and advancing the first core cover web in a machine direction, the first core cover web having side edges extending in the machine direction, with a first core cover width being defined in a cross-machine direction between the side edges of the first core cover web, the cross machine direction being perpendicular to the machine direction;

reducing the width of the first core cover web, by introducing at least one pleat in the first core cover web, the at least one pleat extending in the machine direction between the side edges of the first core cover web and forming a pleated first core cover web having a second core cover width between the side edges of the pleated first core cover web, the second core cover width being smaller than the first core cover width;

applying an adhesive to the first surface of the pleated first core cover web;

advancing the pleated first core cover web onto a mat-forming surface of a mat-former, the mat-former having a recess arranged in the mat-forming surface, the recess having an air-permeable bottom surface and comprising at least one channel-forming element, the at least one channel-forming element being arranged on the bottom surface of the recess and protruding from the bottom surface of the recess;

bringing the pleated first core cover web into conformance with the recess and the at least one channel-forming element on the bottom surface of the recess, with the second surface of the first core cover web facing the bottom surface of the recess and causing the pleat in the first core cover web to at least partially unfold at the at least one channel-forming element;

applying absorbent material on the first surface of the first core cover web in the recess;

providing a second core cover web having a first surface and a second surface;

applying an adhesive on the first surface of the second core cover web;

applying the second core cover web to the first core cover web and to the absorbent material arranged on the first core cover web;

forming an absorbent laminate comprising the absorbent material, the second core cover web and the first core cover web, by pressing together the second core cover web; and forming individual absorbent cores by severing the absorbent laminate in the cross-machine direction.

Each individual absorbent core formed by the method as disclosed herein comprises absorbent material sandwiched between a portion of the second core cover web and a portion of the first core cover web.

The one or more pleats which are formed in the first core cover web before advancing the first core cover web onto the mat-forming surface serve to reduce the stress in the first core cover material as the first core cover material is applied to the mat-forming surface and brought into conformance with the recess in the mat-forming surface and the at least one channel-forming element on the bottom surface of the recess. Thereby, the stress in the first core cover web is reduced and the conformability of the core cover web to the channel-forming element or elements is improved at the same time as the risk for tearing of the first core cover web is reduced or even eliminated.

The pleats in the pleated first core cover web are at least partly unfolded when the pleated first core cover web is brought into conformance with the profiled bottom of the mat-forming recess on the mat-forming surface. The pleats may even be completely obliterated so that they are generally not visible in the final core in an area of the core where channels are formed.

In the mat-forming process vacuum is applied to the air permeable recess in the mat-forming surface to suck the first core cover web into the recess in the mat-forming surface and to cause the first core cover web to be brought into conformance with the channel-forming element or elements at the bottom of the continuous recess.

In the method as disclosed herein, two or more pleats may be introduced in the first core cover web, such as three or more pleats or four or more pleats. Each pleat may correspond to a channel forming element in the mat-forming recess or a pair of pleats may correspond to a channel forming element in the recess arranged in the mat-forming surface.

A pleat as used herein is formed by two folds created in the first core cover web and having the cross-sectional shape of a Z or an inverted Z. Two pleats arranged side by side and being constituted by a Z-shaped pleat and an inverted Z-shaped pleat will together assume an $\Omega$-shaped configuration.

The pleating of the first core cover web may reduce the width of the first core cover web such that the second core cover width may be 65% to 97% of the first core cover width. The width of all pleats together may be 3% to 35% of the core width.

In the method as disclosed herein, the mat-former may comprise a rotating mat-forming drum, the mat-forming surface being a peripheral surface of the mat-forming drum with the recess being arranged in the peripheral surface of the mat-forming drum.

Alternatively, the mat-former may be a moving conveyor with a mat-forming surface in which the recess is arranged.

The channel-forming element or elements may form corresponding areas in the absorbent material which are free or substantially free from absorbent material, such that the first and second core cover webs can be brought in direct contact with each other and be bonded together in the absorbent material free area or areas. Thereby, distinct channels may be formed in the absorbent core along the attachments between the first and second core cover webs.

The attachments between the second core cover web and the first core cover web which are arranged along the channel forming elements stabilize the absorbent core and prevent absorbent material from moving freely and becoming redistributed in an uncontrolled and undesired manner in the space delimited by the first core cover layer and the second core cover layer.

During use of an absorbent article comprising an absorbent core produced according to the method as disclosed herein and comprising an upper core cover layer formed from one of the first or second core cover webs and a lower core cover layer formed from the other of the first and second core cover webs, the absorbent core will absorb body fluid and swell. The bonds between the upper core cover layer and the lower core cover layer in the absorbent core, constitute restriction means which limit swelling in a thickness direction of the absorbent core by prohibiting the upper core cover layer and the lower core cover layer from freely moving away from each other. However, the unfolded pleat or pleats in the upper or lower core cover layer decrease(s) the restrictive forces exerted on the absorbent material which is entrapped between the upper core cover layer and the lower core cover layer and provide(s) the absorbent core with an improved swelling capacity and thereby improves utilization of the absorption capacity of the absorbent material.

After application of adhesive to the second core cover web, the second core cover web may be advanced onto a rotating wheel with the second surface of the second core cover web facing the rotating wheel. The first surface of the second core cover web may be attached to the first surface of the first core cover web and to the absorbent material arranged on the first core cover web in the recess in the mat-forming surface of the mat-former by pressing together the second core cover web and the first core cover web in a nip between the rotating wheel and the mat-forming surface.

As set out herein, the mat-forming surface may be a mat-forming surface on a rotating mat-forming drum or a mat-forming surface on a moving conveyor.

The attachment between the upper and first core cover webs and the absorbent core may alternatively be performed in a stand-alone unit after the mat-former.

In the method as disclosed herein, the recess in the mat-forming surface may be a continuous recess. The recess may be a continuous recess formed in the peripheral surface of a mat-forming drum such that the continuous recess extends around a circumference of the mat-forming drum.

The at least one channel-forming element at the bottom of a continuous recess may consist of 2 to 15-element parts, the element parts being equidistantly distributed around the circumference of the mat-forming drum. When two channel-forming elements are arranged at the bottom of the continuous recess, the element parts of the two channel-forming elements are arranged in 2 to 15 pairs which are equidistantly distributed around the circumference of the mat-forming drum. After forming the absorbent laminate comprising the upper and first core cover webs and the absorbent core sandwiched therebetween, the absorbent laminate is severed in the cross-machine direction between the element parts in the step of forming individual absorbent cores.

The number of channel-forming element parts corresponds to the number of cores formed on the mat-forming drum during one revolution of the mat-forming drum.

Alternatively, the recess in the peripheral surface of the mat-forming drum may be one of a plurality of recesses in the peripheral surface of the mat-forming drum.

In the method as disclosed herein, two or more channel-forming elements may be arranged side-by-side on the bottom surface of the recess in the mat-forming surface, each of the two or more channel-forming elements extending in the machine direction.

In the method as disclosed herein, the absorbent material may comprise cellulose pulp fibers and superabsorbent material. The cellulose pulp fibers and the superabsorbent material may be applied as a mixture on the first surface of the first core cover web the recess in the mat-forming surface. The mixture of cellulose pulp fibers and superabsorbent material may be a uniform mixture. The superabsorbent material may constitute from 5% by weight to 80% by weight of the mixture.

In the method as disclosed herein, the adhesive may be uniformly distributed over the first surface of the pleated first core cover web. The adhesive may be uniformly distributed over the first surface of the second core cover web.

As the adhesive is applied after formation of the pleats, no adhesive is applied inside the pleats. Thereby, a uniform application of adhesive on the first surface of the pleated first core cover web, results in the adhesive being selectively placed on the first surface of the core cover web after unfolding of the first core cover web.

The adhesive may be selectively distributed over the first surface of the first core cover web by applying the adhesive to the first surface of the first core cover web after pleating of the first core cover web and/or by selectively applying adhesive to the first core cover web before pleating of the first core cover web. Selective application of the adhesive is made such that no adhesive is applied in an area of the first core cover web corresponding to the location of the at least one channel-forming element, allowing the pleat or pleats which are formed in the first core cover web to be un-folded over the at least one channel-forming element.

The adhesive may be selectively distributed over the first surface of the second core cover web to affect bonding only where the second core cover web is in contact with the first core cover web. Furthermore, a higher concentration of adhesive may be applied to the first surface of the second core cover web in an area corresponding to the location of the at least one channel-forming element than in other parts of the second core cover web.

The adhesive may be applied to the first and second core cover webs by any suitable method as known in the art, such as slot-coating, spraying and melt-blowing.

The disclosure further pertains to an absorbent core which can be produced according to the method as disclosed herein and involving reducing the width of a first core cover web by introducing at least one pleat in the first core cover web and forming a pleated first core cover web, applying an adhesive to the pleated first core cover web, bringing the pleated first core cover web into conformance with a recess arranged on a mat-former, the recess comprising at least one channel-forming element arranged on a bottom surface of the recess and causing the pleat in the first core cover web to at least partially unfold at the at least one channel-forming element, applying absorbent material on the first core cover web in the recess, applying an adhesive on a second core cover web, applying the second core cover web to the first core cover web and to the absorbent material arranged on the first core cover web, forming an absorbent laminate comprising the absorbent material, the second core cover web and the first core cover web by pressing together the second core cover web and the first core cover web, and forming individual absorbent cores by severing the absorbent laminate.

In an absorbent core as disclosed herein, the first core cover web may form an upper core cover layer and the second core cover web may form a lower core cover layer. Alternatively, the first core cover web may form a lower core cover layer and the second core cover web may form an upper core cover layer.

The absorbent core has a length in a longitudinal direction and a width in a transverse direction, perpendicular to the longitudinal direction, the absorbent core comprising an upper core cover layer and a lower core cover layer and absorbent material sandwiched between the upper core cover layer and the lower core cover layer and comprising at least one channel in the absorbent material. The absorbent core comprises a first part and a second part as seen in the longitudinal direction, the at least one channel is completely arranged in the first part of the absorbent core, wherein one or more pleats are arranged in the upper core cover layer or in the lower core cover layer in the second part of the absorbent core, the one or more pleats extending in the longitudinal direction.

The folds which are arranged in the upper or lower core cover layer form an expandable pleat or pleats in the core cover layer, providing the absorbent core with an improved ability to accommodate a swelling absorption material such as a mixture of cellulose fibres and superabsorbent material. The unfolded pleat or pleats increase the available swelling room between the upper core cover layer and the lower core cover layer within the area of the core where the at least one channel is arranged. As the absorbent material in the absorbent core absorbs liquid and swells, the unfolded pleat or pleats in the lower core cover layer allow the absorbent material to expand with less restriction than in previously known absorbent cores. The unfolded pleats provide expansion room in a thickness direction of the absorbent core which is generally perpendicular to the length and width directions of the absorbent core. The expansible upper or lower core cover layer allows the at least one channel in the absorbent core to remain intact or at least substantially intact during swelling of the absorbent material in the absorbent core. When the absorbent core is incorporated into an absorbent article the at least one channel may retain its liquid acquisition and distribution properties throughout a use of the absorbent article even if the absorbent material in the absorbent core absorbs liquid and swells.

The absorbent core may further comprise a third part, as seen in the longitudinal direction of the core, the first part of the absorbent core being arranged between the second part and the third part of the absorbent core and wherein one or more pleats are arranged in the upper core cover layer or in the lower core cover layer in the third part of the absorbent core, the one or more pleats in the upper or lower core cover layer in the third part of the absorbent core being aligned with corresponding pleats of the one or more pleats in the upper or lower core cover layer in the second part of the absorbent core.

When referring to dimensions of the components in the absorbent articles and the absorbent cores as disclosed herein the dimensions are determined when the absorbent articles and the absorbent cores are in a dry state, i.e., before having absorbed any liquid, unless explicitly stated that the dimensions are determined in a wet state, after absorption of liquid.

The upper and lower core cover layers may be constituted by nonwoven materials. Suitable nonwoven materials may e.g., be spunbond nonwoven materials or nonwoven materials comprising combinations of spunbond and meltblown layers, such as in an SMS configuration. The nonwoven materials may have a basis weight in the order of 6 g/m$^2$ to 12 g/m$^2$.

The core cover layers may be co-terminus or generally co-terminus along the side edges of the absorbent core.

The absorbent material may comprise or consists of a mixture of cellulose pulp fibers and superabsorbent material. The mixture may be a generally uniform mixture or may contain different proportions of superabsorbent and pulp fibers in different parts of the absorbent core. By way of example, the proportion of superabsorbent material may be higher in a longitudinally intermediate portion of the absorbent core, corresponding to the first part of the absorbent core where the channel or channels are arranged, and may be lower at an end portion of the absorbent core corresponding to one or both of the first and third parts of the absorbent core, as disclosed herein.

The superabsorbent material may be present in the mixture in an amount of from 5% by weight to 80% by weight of the mixture.

The absorbent core may have a rectangular shape with side edges extending in the longitudinal direction and end edges extending in the transverse direction and wherein the lower core cover layer has a greater width in the transverse direction than the upper core cover layer, the width of the core cover layers being the width of the core cover layers in an unfolded, flat-out state.

The absorbent core may have a rectangular shape, or any other suitable shape as known in the art such as hourglass shape, dogbone shape T-shape, H-shape, etc. A rectangular absorbent core may have the advantage of being easy to manufacture and enclose in a core cover.

Superabsorbent materials suitable for use in the absorbent cores as disclosed herein are well known in the field of absorbent articles and are constituted by water-swellable and water-insoluble material which can absorb large quantities of fluid upon formation of a hydrogel. The absorbent core may contain superabsorbent material in the form of fibers or particles of absorbent polymer material. For example, the superabsorbent material may be surface cross-linked, partially neutralized polyacrylates. The superabsorbent material, e.g., the superabsorbent fibers or particles, may be mixed with other absorbent or liquid uptake material or materials, such as cellulose fluff pulp.

BRIEF DESCRIPTION OF THE DRAWINGS

The method, and the absorbent cores and absorbent articles as disclosed herein will be further explained hereinafter with reference to the appended drawings wherein:

FIG. 2 shows a top view of a first core cover web being applied to a mat-forming surface in a method according to prior art;

FIG. 3 shows a cross section through the first core cover web and the mat-forming surface in FIG. 2, taken along the line III-III;

FIG. 4 shows a top view of a first core cover web being applied to a mat-forming surface in a method as disclosed herein;

FIG. 5 shows a cross section through the first core cover web and the mat-forming surface in FIG. 4, taken along the line V-V;

DETAILED DESCRIPTION

Different aspects of the present disclosure will be described more fully hereinafter with reference to the enclosed drawings. The embodiments disclosed herein can, however, be realized in many different forms and should not be construed as being limited to the aspects set forth herein. It is to be understood that although the absorbent hygiene article shown in the Figures is a pant-type absorbent article, the method as disclosed herein is applicable when forming any type of disposable absorbent hygiene article as disclosed herein comprising an absorbent core with swellable absorbent material sandwiched between an upper core cover layer and a lower core cover layer. The absorbent core as described herein may be used in any disposable absorbent article for absorbing urine, feces and/or vaginal discharges.

It is to be understood that the drawings are schematic and that individual components, such as layers of material are not necessarily drawn to scale.

Figure 1:
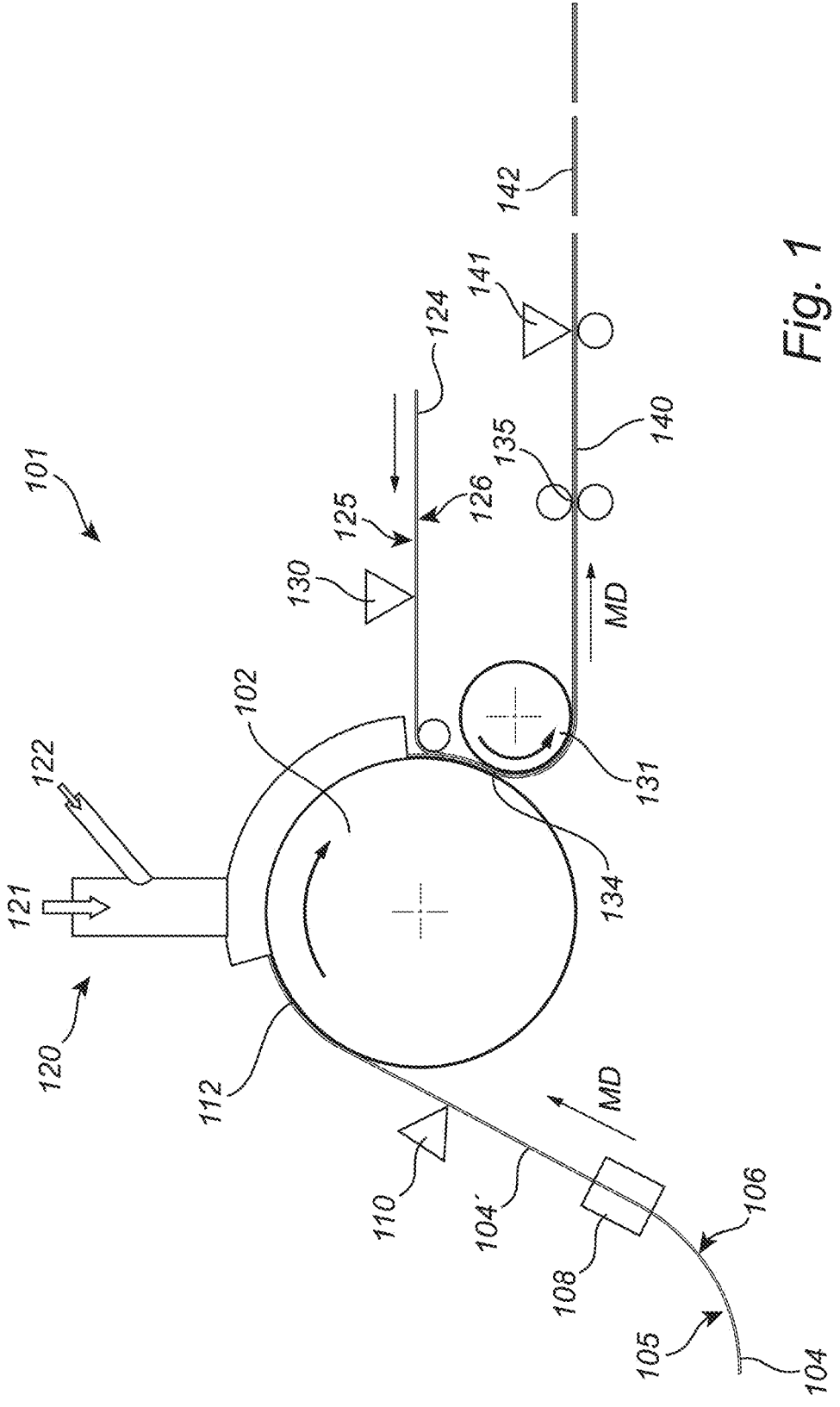
FIG. 1 shows a schematic view of a method as disclosed herein.

With initial reference to FIG. 1, there is shown a schematic representation of a method for producing absorbent cores for use in disposable absorbent hygiene articles.

The method which is shown in FIG. 1 is performed using a mat-former 101 comprising a rotating mat-forming drum 102. A first core cover web 104 having a first surface 105 and a second surface 106 is advanced in a machine direction MD.

The first core cover web 104 is passed through a pleat forming unit 108 where two pleats 109 are formed in the first core cover web 104, as seen in FIG. 4, the pleats 109 extending in the MD between the side edges of the first core cover web 104. Although two pleats are shown and described herein, it is to be understood that any suitable number of pleats may be formed in the first core cover web 104 by the pleat forming unit 108, such as one pleat, 3 pleats, or more. By pleating the first core cover web 104, the width w of the first core cover web 104 is reduced such that a second width 2 of the pleated first core cover web 104' is smaller than the first width w1 of the non-pleated first core cover web 104. The widths w1, w2 of the non-pleated and pleated first core cover web 104, 104' is measured between the side edges 111 of the first core cover web 104 in a cross machine direction CD perpendicular to the MD, as shown in FIG. 4.

In a next step, an adhesive, such as a liquid adhesive, is applied to the first surface 105 of the pleated first core cover web 104' by a first adhesive applicator 110. After adhesive application, the pleated first core cover web 104' is advanced onto a mat-forming surface 112 on the rotating mat-forming drum 102 of the mat-former 101. The mat-forming drum 102 has a recess 113 arranged in the mat-forming surface 112, see FIGS. 4 and 5, the recess 113 having a bottom surface 114 and comprising two channel-forming elements 115. The channel-forming elements 115 are arranged on the bottom surface 114 of the recess 113 and protrude from the bottom surface 114 of the recess 113. As for the pleats 109 in the first core cover web 104, the number of channel-forming elements at the bottom surface 114 of the recess 113 may be varied as disclosed herein. Accordingly, a single channel-forming element may be used, or more than two channel-forming elements may be used. The number of channel-forming elements 115 may correspond to the number of pleats 109 in the first core cover web 104 and the location of the pleats 109 in the first core cover web 104 may be synchronized with the placement of the channel-forming elements 115.

The pleated first core cover web 104' is subsequently sucked into the recess 113 by a vacuum force V, which is applied from inside the rotating mat-forming drum 102 through the air permeable bottom surface 114 of the recess 113.

As is illustrated by FIG. 5, the pleated first core cover web 104' as seen at the top of the figure, is moved into the recess 113, in the direction of the arrow A, and is brought to conform to the shape of the recess 113 and to the two channel-forming elements 115 in the recess 113, with the second surface 106 of the first core cover web facing the bottom surface 114 of the recess 113. During the process, the pleats 109 in the core cover web 104 are caused to unfold and cover the bottom 114 of the recess as well as the channel-forming elements 115, as seen in the lower portion of FIG. 5. The pleated core cover web 104' is drawn into the recess 113 by the vacuum force V applied from inside the rotating mat-forming drum 102 and causing the pleats 109 in the pleated first core cover web 104' to unfold at the channel-forming elements 115 and to readily conform to the shape of the channel-forming elements 115 due to the excess material which becomes available as the pleats 109 unfold. The pleats in the first core cover web 104 allows the first core cover web 104 to conform to the shape of the protruding channel-forming elements 115 without undue stretching or tensioning of the first core cover web 104.

This differs from the prior art application of a first core cover web 104 to a recess 113 having channel-forming elements 115, as shown in FIGS. 2 and 3. In the prior art application of a first core cover web 104, the first core cover web 104 is sucked into the recess 113 by the vacuum force V, causing stress to build up in the material at the relatively distinct edges and corners of the channel-forming elements 115. The tension in the first core cover web material may give rise to tearing or piercing of the first core cover web. In addition, the prior art first core cover web 104 has a lower ability to conform to the shape of the recess 113, implying that the available space for filling absorbent material in the recess is reduced by non-conforming parts of the first core cover web 104, as is illustrated in FIG. 3.

Absorbent material is then applied on the first surface 105 of the first core cover web in the recess 113 on the mat-forming surface 112 of the rotating mat-forming drum 102. In FIG. 1, the application of absorbent material is illustrated by an air-laying unit 120 in which air-entrained wood pulp 121 is mixed with superabsorbent material 122, such as superabsorbent particles or fibres and the mixture is drawn into to the recess 113 which is clad with the first core cover web 104.

After application of the absorbent material, a second core cover web 124 having a first surface 125 and a second surface 126 is supplied and an adhesive, such as a liquid adhesive is applied to the first surface 125 of the second core cover web 124 by a second adhesive applicator 130. The second core cover web 124 is advanced onto a rotating wheel 131 with the second surface 126 of the second core cover web 124 facing the rotating wheel 131. The second core cover web 124 is applied to the mat-forming surface 112 of the rotating mat-forming drum 102 by the rotating wheel 131 and is brought to cover the first core cover web 104 and the absorbent material 121, 122 arranged on the first core cover web 104 in the recess 113.

The first surface 125 of the second core cover web 124 is attached to the first surface 105 of the first core cover web 104 and to the absorbent material 121, 122 arranged on the first core cover web 102 in the recess 113 in the mat-forming surface 112 of the mat-forming drum 102 by pressing together the second core cover web 124 and the first core cover web 104 in a nip 135 between two rollers, forming an absorbent laminate 140 comprising the absorbent material 121, 122, the second core cover web 124 and the first core cover web 104. Pressing together the second core cover web 124 and the first core cover web 104 brings the core cover webs in direct contact or substantially direct contact with each other in the generally absorbent material free areas created at the channel-forming elements 115 and in coinciding areas of the second core cover web 124 and the first core cover web 104 located outside the recess 113.

Alternatively, or in addition thereto, formation of the absorbent laminate 140 may involve pressing together the second core cover web and the first core cover web in the nip 134 between the rotating wheel 131 and rotating mat-forming drum 102.

After forming the absorbent laminate 140, individual absorbent cores 142 are formed by severing the absorbent laminate 140 in the cross-machine direction in a cutting unit 141.

Although the method as disclosed herein has been illustrated using a mat-former 101 with a rotating mat-forming drum 102, it is to be understood that the method as disclosed herein is equally applicable to mat-forming on a moving conveyor.

The recess 113 in the mat-forming surface 112 of the mat-forming drum 102 may be a continuous recess extending around the full circumference of the mat-forming drum 102 or the recess may be one of a plurality of recesses being equidistantly distributed around the circumference of the mat-forming drum 102.

As disclosed herein, each channel-forming element 115 in a continuous recess may consist of a plurality of element parts, the element parts being equidistantly distributed around the circumference of the mat-forming drum 102. When two channel-forming elements are arranged side-by side, the element parts are arranged in pairs around the circumference of the mat-forming drum 102. When severing the absorbent laminate 140 to form individual absorbent cores 142, the absorbent laminate 140 is severed in the cross-machine direction CD between the element parts. Accordingly, the number of channel-forming element parts of each channel-forming element 115 corresponds to the number of cores formed on the mat-forming drum during one revolution.

The adhesive may be uniformly distributed over the first surface 105 of the pleated first core cover web 104'. Likewise, the adhesive may be uniformly distributed over the first surface of the second core cover web 124.

Alternatively, the adhesive may be selectively distributed on one or both core cover web 104, 124 to create any desired bonding pattern.

Figure 6:
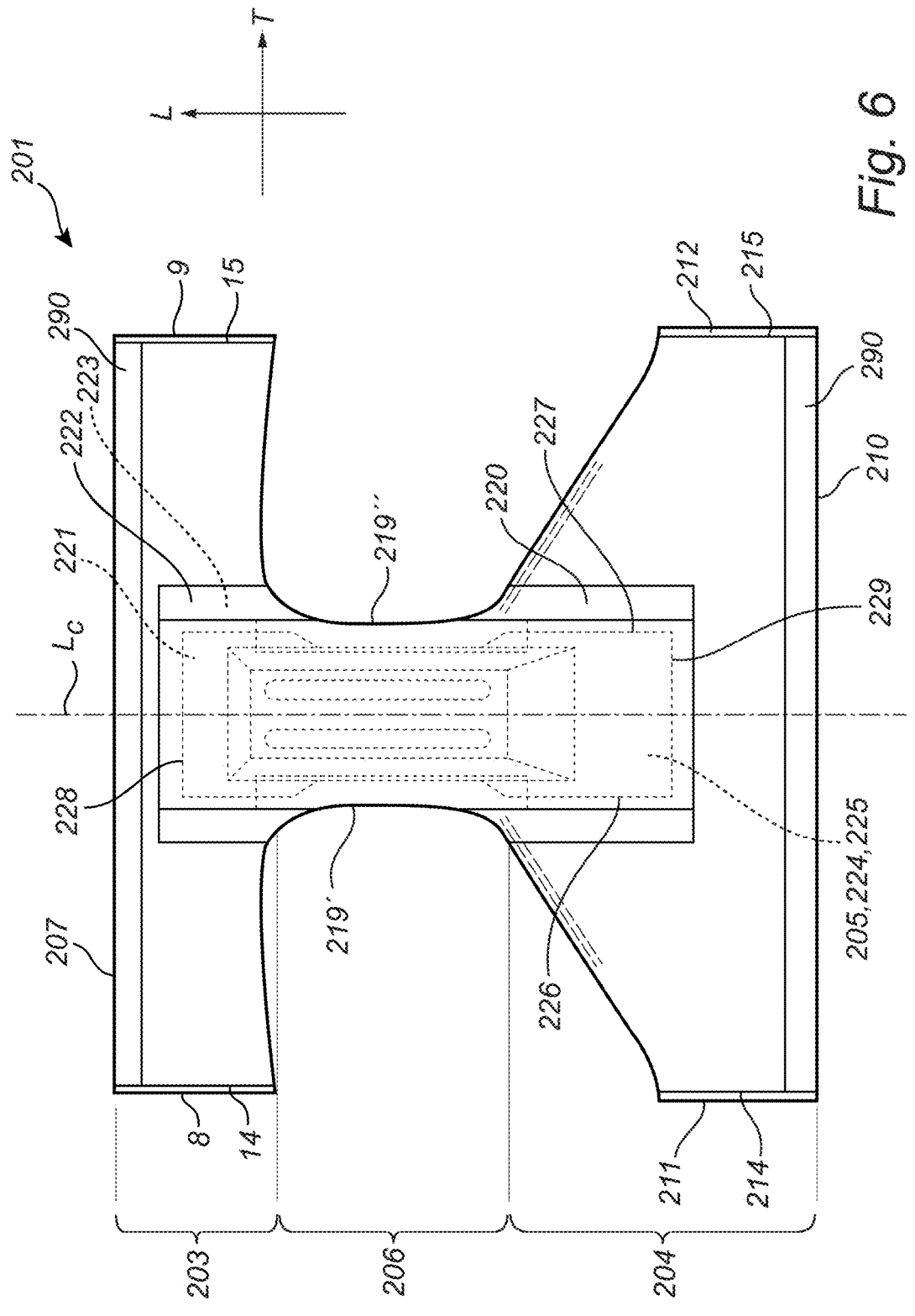
FIG. 6 shows a planar view of a stretched-out absorbent pant-type article with an absorbent assembly and with open side seams, as seen from an inner surface of the pant-type article.

With reference to FIG. 6, the pant-type article which is shown in the figure is a simplified article, and it is to be understood that the article may contain further features, such as barrier cuffs, a wetness indicator, etc. It is also to be understood that the waist elastic disclosed herein is optional or any other suitable type of waist elastic may be used. The side seams may be reclosable side seams, and the pant-type article may be provided with fastener elements to provide reclosability of the side seams.

The pant-type article 201 in FIG. 6 in the form of a pant-type incontinence article for adult users. The pant-type article 201 is shown in FIG. 6 in an unfolded and flat condition with all elastic elements in a fully extended state. The pant-type article has a longitudinal direction L and a transverse direction T, perpendicular to the longitudinal direction with a longitudinal centerline Lc extending in the longitudinal direction L.

The pant-type article 201 is seen from the inner surface which is the surface which will be facing a wearer's body when the article is being worn and which is opposite the outer, garment-facing surface of the pant-type article 201.

The pant-type article 201 comprises a front portion 203, a rear portion 204 and an absorbent assembly 220 located in a crotch portion 206 of the pant-type article 201 and extending in the longitudinal direction L forward in over the front portion 203 and rearward in over the rear portion 204. The absorbent assembly 220 in the pant-type article shown in the figures is a separately produced component which comprises an absorbent core 221 comprising absorbent material being sandwiched between an upper core cover layer 224 and a lower core cover layer 225. The absorbent core 221 is further enclosed between a liquid permeable topsheet 222 and a liquid barrier layer 223. The absorbent core 221 is arranged between the topsheet 222 and the liquid barrier layer 223 with the upper core cover layer 224 facing the liquid topsheet 222 and the lower core cover layer 225 facing the liquid barrier layer 223.

The absorbent articles as disclosed herein are not limited to absorbent articles having the absorbent core applied to the article as a component of a pre-fabricated absorbent assembly which already comprises a topsheet and a liquid barrier layer.

The front portion 203 has a front waist edge 207 extending in the transverse direction T and a pair of front side edges 208, 209 extending in the longitudinal direction L. The rear portion 204 has a rear waist edge 210 extending in the transverse direction T and a pair of rear side edges 211, 212 extending in the longitudinal direction L.

The first front side edge 208 is joined to the first rear side edge 211 in a first side seam 214 and the second front side edge 209 is joined to the second rear side edge 212 in a second side seam 215 to create the pant-type article 201 having a waist opening 216, a first leg opening 217 and a second leg opening 218, as shown in FIG. 9.

The side seams 214, 215 of the pant-type article 201 may be generally band-shaped joins which are formed by ultrasonic welding or thermowelding. To have sufficient strength to withstand the forces to which the pant-type article 201 is exposed during donning of the article and to allow sufficient production tolerances, the side seams commonly have a width in the order of 5 to 10 millimeters. It is also known to make side seams having a width less than 5 mm.

It is generally desired that a soiled pant-type article can be easily removed without having to pull the article down over the legs of a user. Therefore, the side seams are commonly made such that they are breakable by manual force to allow a user or a caregiver to pull apart the side seams before removing a soiled pant-type article.

The waist opening 216 is defined by the front waist edge 207 and the rear waist edge 210. A first leg edge 219' defines the first leg opening 217 and a second leg edge 219" defines the second leg opening 218.

Figure 7:
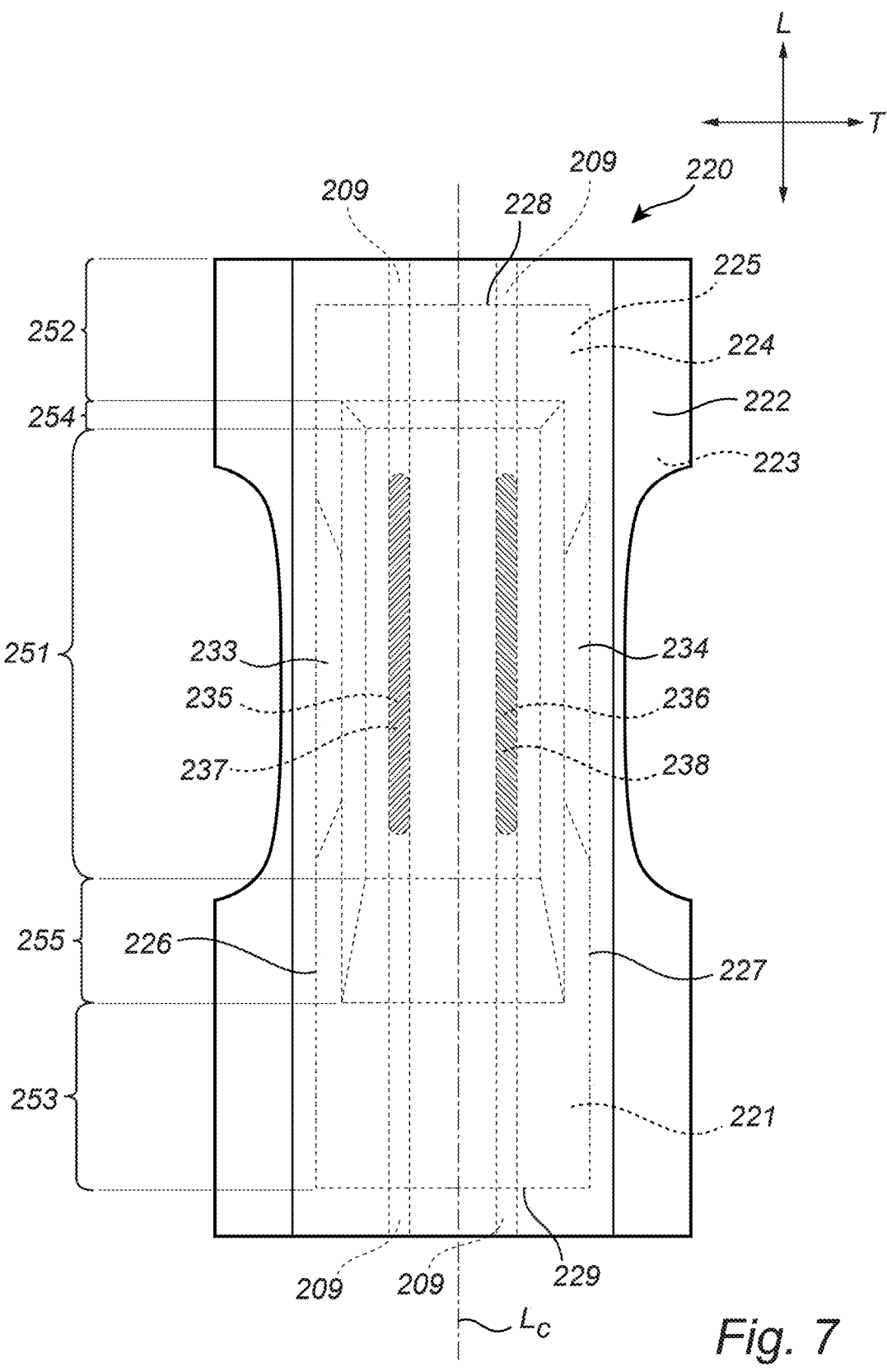
FIG. 7 shows an enlarged view of the absorbent assembly in the pant-type article in FIG. 6 with an absorbent core enclosed in a core cover.
Figure 8:
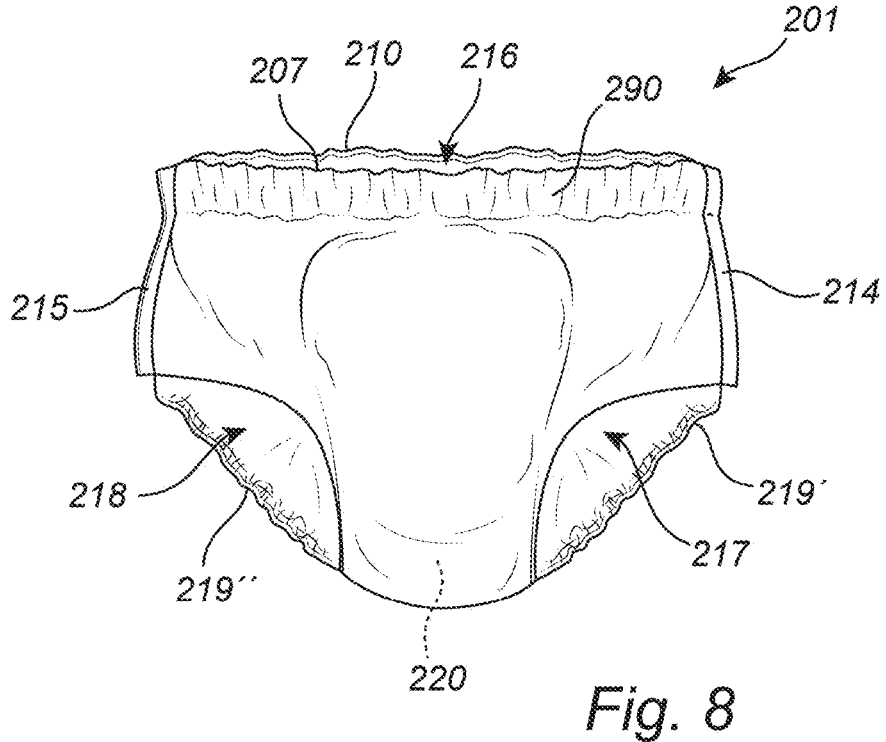
FIG. 8 shows the pant-type article in FIG. 6 with the side seams closed and in a non-stretched out condition, as it appears before use.

The absorbent assembly 220 is shown in greater detail in FIG. 7 and has a generally hourglass shape. The absorbent core 221 which is enclosed between the liquid permeable topsheet 222 and the liquid barrier layer 223 has a rectangular shape with a first side edge 226 and a second side edge 227, a first end edge 228 and a second end edge 229. The first side edge 226 and the second side edge 227 of the absorbent core 221 have a main extension in the longitudinal direction L and the first end edge 228 and the second end edge 229 have a main extension in the transverse direction T.

The absorbent core 221 has a length in the longitudinal direction L and a width in the transverse direction T. The absorbent core comprises the upper core cover layer 224 and the lower core cover layer 225 and absorbent material sandwiched between the upper core cover layer 224 and the lower core cover layer 225.

The absorbent core 221 may be divided into a first core part 251, a second core part 252 and a third core part 253, with the first core part 251 being arranged between the second core part 252 and the third core part 253. The first core part 251 is a central part 251 of the absorbent core 221, the second core part 252 is a front end part 252 of the absorbent core 221 and the third core part 253 is a rear end part 253 of the absorbent core 221, as seen in the longitudinal direction L of the absorbent core 221.

Two pleats 209 are arranged in the lower core cover layer 225 in each of the second core part 252 and the third core part 253. The pleats 209 in the third or rear part 253 of the absorbent core 221 are aligned with the corresponding pleats 209 in the second or front part 252 of the absorbent core 221. This arrangement is a result of the manufacturing process for the absorbent core 221 which is described herein, e.g., with reference to FIGS. 1, 4 and 5 and which produces an absorbent core having unfolded pleats in the first core part 251 where longitudinally extending channels 235, 236 are arranged and pleats 209 remaining in parts 252, 253 of the core 221 where no channels have been formed.

In the absorbent core 221 which is shown in the figures, the first core cover web 104 forms the lower core cover layer 225. However, it is to be understood that it is equally viable to use the first core cover web 104 as the upper core cover layer in an absorbent core as disclosed herein. In such case, the remaining pleats will be in the upper core cover layer.

When measuring the width of the upper core cover layer 224 and the lower core cover layer 225 in an unfolded flat-out state, the lower core cover layer in the absorbent core 221 shown in the figures, has a greater width in the transverse direction T than the upper core cover layer 224.

A first channel 235 and a second channel 236 are arranged in the absorbent core 221 and extend in the longitudinal direction L on either side of the longitudinal center line Lc and at a distance from each of the first and second side edges 226, 227 of the absorbent core 221. The channels 235, 236 are free or substantially free from absorbent material. The first and second channels are completely arranged in the first, central part 251 of the absorbent core 221.

The upper core cover layer 224 and the lower core cover layer 225 are connected to each other by a first side seal 233 extending along the first side edge 226 of the absorbent core 221 and by a second side seal 234 extending along the second side edge 227 of the absorbent core 221. In addition, the upper and lower core cover layers 224, 225 are connected by a first channel seal 237 in the first channel 235 and by a second channel seal 238 in the second channel 236.

The channel seals 237, 238 are permanent seals or substantially permanent seals which do not break under normal use and handling of the absorbent article. Accordingly, the channel seals 237, 238 remain intact or substantially intact even after the absorbent article has absorbed liquid. The side seals 233, 234 may be permanent seals or may be breakable seals with low seal strength such that the side seals 233, 234 break under influence of the forces exerted on the side seals 233, 234 as the absorbent material in the absorbent core 221 absorbs fluid and expands.

As disclosed herein, the side seals 233, 234 and the channel seals 237, 238 are adhesive seals formed by the adhesive applied to the facing surfaces of the second core cover web 124 and the first core cover web 104 in the method as disclosed herein.

Depending on the type and size of absorbent article in which the one or more channels as disclosed herein are arranged, the length of the channels 235, 236 may range from 50 millimeter to 500 millimeter.

In a pant-type absorbent article for incontinent adult users, such as the absorbent article 201 shown in the figures, the channels 235, 236 are preferably arranged in the crotch portion 206 of the article which is the narrow portion of the article which will be placed in the crotch of a user when the article is worn. The narrow crotch portion 206 of an absorbent article is the portion of the article which will receive a major part of excreted body fluid, such as urine. The crotch portion 206 may therefore have good absorption properties in terms of liquid acquisition, liquid distribution, and absorption capacity. The channels 235, 236 in the absorbent core 221 contribute to rapid liquid acquisition and promote fluid distribution by channelling the fluid flow towards the front and rear portions 203, 204 of the absorbent article 201. In the absorbent article 201 which is shown in the figures, the length of the channels 235, 236 substantially corresponds to the length of the crotch portion 206 and may typically be in the order of from 100 millimeter to 250 millimeter.

In wearable incontinence articles such as open diapers and pant-type diapers, the channels will typically have a length in the order of from 30% to 50% of the total length of the absorbent core. In smaller absorbent articles such as incontinence shields and sanitary napkins, the channels may extend almost to the ends of the absorbent core, such as up to 80% of the total length of the absorbent core.

To enhance the absorbent capacity in the narrow crotch portion 206 of the absorbent article 201, the central first part 251 of the absorbent core 221, has a greater thickness than the front end part 252 and the rear end part 253 of the absorbent core 221.

The central part 251 of the absorbent core 221 is shown with a uniform thickness and each of the end parts 252, 253 has a uniform thickness, the central part 251 of the absorbent core 221 being delimited from the end parts 252, 253 by front and rear transition zones 254, 255. The thickness of the absorbent core 221 diminishes linearly from the central part 251 of the absorbent core 221 to the end parts 252, 253 of the absorbent core 221 within the transition zones 254, 255. As is shown in FIG. 7, the pleats 209 are present also in the lower core cover layer 225 also beneath the transition zones 254, 255 as the channels 235, 236 do not extend into the transition zones 154, 255.

In the figures, the absorbent core 221 is shown with a rectangular shape defined by the shape of the core cover layers and the absorbent material between the core cover layers is shown to be arranged in a generally hourglass shape in the L/T plane and a three-dimensional profile in the thickness direction. However, it is to be understood that the absorbent core 221 may be cut to a shape different from a rectangular shape, for example an hourglass shape. Likewise, the absorbent material may be arranged in other configurations than that which is shown in the figures. Accordingly, the three-dimensional profile of the absorbent core which is shown in FIG. 7 is non-limiting to the absorbent cores as disclosed herein and any planar and three-dimensional shape may be used for the overall core and for the absorbent material which is sandwiched between the core cover layers.

In a planar or substantially planar absorbent core, the absorbent capacity in the absorbent core may be different in different parts of the core as a result of different amounts of superabsorbent material being arranged in the different parts of the core.

The absorbent core 221 as disclosed herein may comprise any material suitable for absorbing discharged bodily wastes, such as cellulosic fluff pulp and highly absorbent polymers (super absorbents). The absorbent assembly 220 may comprise further absorbent components, such as tissue layers, absorbent foam materials including hydrogel-foam material, absorbent nonwoven materials, or the like. The absorbent assembly can comprise non-absorbent components such as stiffening elements, shaping elements, binders, etc. Various types of liquid-receiving and liquid distribution elements can also be included in the absorbent assembly.

The absorbent core 221 preferably comprises superabsorbent material, such as superabsorbent material in an amount of from 5% by weight to 80% by weight of the absorbent material, at least in the central part 251 of the absorbent core 221. As set out herein, the superabsorbent content may be lower in the front end part 252 and/or in the rear end part 253 of the absorbent core 221 than in the central part 251 of the absorbent core 221 or may be the same in all parts of the absorbent core 221.

The superabsorbent material is a polymeric material and may be in the form of particles, granules fibers, flakes, etc.

As disclosed herein, the absorbent material in the absorbent core 221 may comprise or consist of a mixture of absorbent cellulose fibers, such as cellulose pulp fibers, and superabsorbent material.

A high amount of superabsorbent material in the absorbent core, makes it possible to produce absorbent articles which are thin and discrete while offering high absorbent capacity and an ability to chemically bind and immobilize absorbed fluid which results in an absorbent article having high leakage security and a dry inner surface even after having absorbed a large amount of fluid.

The superabsorbent material absorbs liquid upon swelling and formation of an aqueous gel. To fully utilize the absorbent capacity of the superabsorbent material, the absorbent article may provide sufficient expansion room for the superabsorbent material. As the absorbent core is entrapped between the upper core cover layer 224 and the lower core cover layer 225 swelling of the superabsorbent material will be limited by the available expansion room between the core cover layers 224, 225.

The liquid permeable topsheet 222 may comprise or consist of a nonwoven material. Other suitable topsheet materials include tow fibers, porous foams, apertured plastic films and laminates and combinations of such materials. The materials which are best suited as topsheet materials are soft and non-irritating to the skin, are readily penetrated by body fluids, and display low rewet.

The liquid barrier layer 223 may consist of a thin plastic film, e. g. a polyethylene or polypropylene film, a nonwoven material coated with a liquid impervious material, a hydrophobic nonwoven material which resists liquid penetration or laminates of plastic film and nonwoven. The liquid barrier layer material may be breathable to allow vapour to escape from the absorbent body, while still preventing liquids from passing through the liquid barrier layer material.

The topsheet and liquid barrier layer may be connected to each other for example by adhesive bonding, gluing or welding by heat or ultrasonically. The topsheet and/or the liquid barrier layer may further be attached to the core cover by any method known in the art, such as adhesive, heat-bonding, welding, etc.

A pant-type article may have a two-part chassis with a crotch panel which is connected to a front panel along a front panel crotch edge, and which is connected to a rear panel along a rear panel crotch edge. The front and rear panels may be made from elastic or elasticized web material or an elastic laminate material, and the crotch panel may be a non-elastic web material or a non-elastic laminate material. Alternatively, a pant-type article may have a unitary chassis having a non-elastic outer or inner cover web extending the full distance between the front waist edge and the rear waist edge, the cover web constituting a non-elastic layer of each of the front portion and the rear portion and constituting a crotch web material in the crotch portion of the pant-type article.

A pant-type article 201 as disclosed herein may have an elastic waist feature 290 arranged along the waist opening 216. An elastic waist feature 290 may be formed by one or more elastic elements extending parallel with the front waist edge 207 and the rear waist edge 210. The elastic waist element or elements may be incorporated in the front portion 203 and the rear portion 204 of the article 201, or may be applied as a separate waistband which is attached to the front 2 waist edge 207 and the rear waist edge 210. The pant-type article 201 which is shown in the Figures has an elastic waist feature 290 which extends around the full circumference of the waist opening 216. However, an elastic waist feature may be arranged along only a part of the waist opening, such as along only the rear waist edge, along only the front waist edge or along a part of one or both the front and the rear waist edge which part has a length which is less than the full length of the corresponding waist edge.

The elastic material in elastic elements arranged along the leg openings 217, 218 and the waist opening 216 as disclosed herein may be any suitable elastic material such as natural or synthetic rubber, thermoplastic elastomers, such as thermoplastic polyurethane or styrene block co-polymers or elastane, also referred as to spandex (polyurethane-polyurea copolymer). The elastic elements may be of the elastane type that is available under the trade name "LYCRA", but any suitable elastic thread may be used.

The upper and lower core cover layers may be constituted by nonwoven materials, as disclosed herein.

The nonwoven materials used in the absorbent articles as disclosed herein may comprise thermoplastic material. The nonwoven web-materials will typically be incorporated in joins and seams in the absorbent article and it may be desirable that the nonwoven webs be weldable by heat or by ultrasonic welding processes. Examples of suitable polymers for use in the fibrous nonwoven webs as disclosed herein are polyethylene polypropylene and other polyolefin homopolymers and copolymers and polyesters. The weldable nonwoven webs have a high content of thermoplastic component and preferably contain at least 50% thermoplastic fibers and more preferably at least 80% thermoplastic fibers.

The invention claimed is:

1. A method of manufacturing an absorbent core for a disposable absorbent hygiene article, the method comprising;

providing a first core cover web having a first surface and a second surface and advancing the first core cover web in a machine direction, the first core cover web having side edges extending in the machine direction, with a first lower core cover width being defined between the side edges of the first core cover web, in a cross-machine direction, the cross machine direction being perpendicular to the machine direction;

introducing at least one pleat in the first core cover web, the at least one pleat extending in the machine direction between the side edges of the first core cover web and forming a pleated first core cover web having a second core cover width between the side edges of the pleated first core cover web, the second core cover width being smaller than the first core cover width;

applying an adhesive to the first surface of the pleated first core cover web;

advancing the pleated first core cover web onto a mat-forming surface of a mat-former, the mat-former having a recess arranged in the mat-forming surface, the recess having an air permeable bottom surface and comprising at least one channel-forming element, the at least one channel-forming element being arranged on the bottom surface of the recess and protruding from the bottom surface of the recess;

bringing the pleated first core cover web into conformance with the recess and the at least one channel-forming element on the bottom surface of the recess with the second surface of the first core cover web facing the bottom surface of the recess and causing the pleat in the first core cover web to at least partially unfold at the at least one channel-forming element;

applying absorbent material on the first surface of the first core cover web in the recess;

providing a second core cover web having a first surface and a second surface;

applying an adhesive on the first surface of the second core cover web;

applying the second core cover web to the first core cover web and to the absorbent material arranged on the first core cover web;

forming an absorbent laminate comprising the absorbent material, the second core cover web and the first core cover web, by pressing together the second core cover web and the first core cover web; and forming individual absorbent cores by severing the absorbent laminate in the cross-machine direction.

2. A method according to claim 1, wherein two or more pleats are introduced in the first core cover web.

3. A method according to claim 1, wherein the second core cover width is 65% to 97% of the first core cover width.

4. A method according to claim 1, wherein the mat-former comprises a rotating mat-forming drum and the mat-forming surface is a peripheral surface of the mat-forming drum, the recess being arranged in the peripheral surface of the mat-forming drum.

5. A method according to claim 4, wherein the recess in the peripheral surface the mat-forming drum is a continuous recess extending around a circumference of the mat-forming drum.

6. A method according to claim 5, wherein each at least one channel-forming element consists of 2 to 15 element parts, the element parts being equidistantly distributed around the circumference of the mat-forming drum, and wherein the absorbent laminate is severed in the cross-machine direction between the element parts in the step of forming individual absorbent cores.

7. A method according to claim 4, wherein the recess in the peripheral surface of the mat-forming drum is one of a plurality of recesses in the peripheral surface of the mat-forming drum.

8. A method according to claim 1, wherein two or more channel-forming elements are arranged side-by-side on the bottom surface of the recess in the mat-forming surface, each of the two or more channel-forming elements extending in the machine direction.

9. A method according to claim 1, wherein the absorbent material comprises cellulose pulp fibers and superabsorbent material.

10. A method according to claim 9, wherein the cellulose pulp fibers and the superabsorbent material are applied as a mixture on the first surface of the first core cover web in the recess in the mat-forming surface.

11. A method according to claim 10, wherein the mixture of cellulose pulp fibers and superabsorbent material is a uniform mixture, the superabsorbent material constituting from 5% by weight to 80% by weight of the mixture.

12. A method according to claim 1, wherein the adhesive is uniformly distributed over the first surface of the pleated first core cover web.

13. A method according to claim 1, wherein the adhesive is selectively distributed over the first surface of the first core cover web, with no adhesive being applied in an area of the first core cover web corresponding to the location of the at least one channel-forming element.

14. A method according to claim 1, wherein the adhesive is uniformly distributed over the first surface of the second core cover web.

15. A method according to claim 1, wherein the adhesive is selectively distributed over the first surface of the second core cover web and/or wherein a higher concentration of adhesive is applied to the first surface of the second core cover web in an area corresponding to the location of the at least one channel-forming element.

* * * * *